United States Patent
Wei et al.

(10) Patent No.: US 12,099,053 B2
(45) Date of Patent: Sep. 24, 2024

(54) METHOD OF TRAINING AI FOR LABEL-FREE CELL VIABILITY DETERMINATION AND LABEL-FREE CELL VIABILITY DETERMINATION METHOD BY TRAINED AI

(71) Applicant: INDUSTRIAL TECHNOLOGY RESEARCH INSTITUTE, Hsinchu (TW)

(72) Inventors: Hsiang-Chun Wei, Hsinchu (TW); Chih-Hsiang Liu, Xinpu Township (TW); Chung-Lun Kuo, New Taipei (TW); Chun-Wei Lo, Taichung (TW); Chia-Hung Cho, Hsinchu (TW); Wei-Hsiung Tsai, Xinpu Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 346 days.

(21) Appl. No.: 17/563,701

(22) Filed: Dec. 28, 2021

(65) Prior Publication Data
US 2023/0160879 A1    May 25, 2023

(30) Foreign Application Priority Data
Nov. 19, 2021  (TW) ................................ 110143123

(51) Int. Cl.
*G01N 33/50* (2006.01)
*G01N 15/1433* (2024.01)
(Continued)

(52) U.S. Cl.
CPC ....... *G01N 33/505* (2013.01); *G01N 15/1433* (2024.01); *G03H 1/0005* (2013.01);
(Continued)

(58) Field of Classification Search
CPC ............. G01N 15/1433; G01N 33/505; G01N 15/1475; G01N 33/50; G01N 15/14;
(Continued)

(56) References Cited

U.S. PATENT DOCUMENTS 6,411,406 B1   6/2002  Kreuzer
11,092,532 B2 *  8/2021  Singh .................. G06V 20/698
(Continued)

FOREIGN PATENT DOCUMENTS

CN    108780032 A    11/2018
TW    I705414 B      9/2020
TW    I726920 B      5/2021

OTHER PUBLICATIONS

TW Notice of Allowance dated Oct. 16, 2023 in application No. 110143123.
(Continued)

*Primary Examiner* — Tuan H Nguyen
(74) *Attorney, Agent, or Firm* — Maschoff Brennan

(57) ABSTRACT

A method of training AI for label-free cell viability determination includes a step of providing a cell sample, a step of obtaining a fluorescence image and a DHM image of the cell sample, a step of determining a first cell viability of the cell sample according to the fluorescence image of the cell sample, a step of labeling the DHM image of the cell sample as a model specifying the first cell viability, and a step of performing AI training by using the model containing the DHM image of the cell sample.

9 Claims, 4 Drawing Sheets

(51) Int. Cl.
*G03H 1/00* (2006.01)
*G03H 1/04* (2006.01)
*G03H 1/08* (2006.01)
*G06T 7/00* (2017.01)

(52) U.S. Cl.
CPC ......... *G03H 1/0443* (2013.01); *G03H 1/0866* (2013.01); *G06T 7/0012* (2013.01); *G03H 2001/0033* (2013.01); *G03H 2001/005* (2013.01); *G06T 2207/10056* (2013.01); *G06T 2207/10064* (2013.01); *G06T 2207/20081* (2013.01); *G06T 2207/20084* (2013.01); *G06T 2207/30024* (2013.01)

(58) Field of Classification Search
CPC .......... G03H 1/0005; G03H 1/00; G03H 1/04; G03H 1/08; G03H 1/0866; G03H 1/0443; G06T 7/0012; G06T 7/00; G06T 2207/30024; G06T 2207/20081; G06T 2207/10056; G06T 2207/20084; G06T 2207/10064
See application file for complete search history.

(56) References Cited

U.S. PATENT DOCUMENTS

| | | | |
|---|---|---|---|
| 11,227,386 B2* | 1/2022 | El-Zehiry | G02B 21/244 |
| 2019/0195774 A1 | 6/2019 | El-Zehiry et al. | |
| 2019/0371425 A1 | 12/2019 | Kuo et al. | |
| 2020/0116617 A1 | 4/2020 | Singh et al. | |
| 2020/0354677 A1* | 11/2020 | Lee | A61K 39/0011 |
| 2021/0142472 A1 | 5/2021 | Mathuis et al. | |

OTHER PUBLICATIONS

TW office action in application No. 110143123 dated Apr. 14, 2023.
Allier et al., "Label-free cell viability assay using lens-free microscopy" Feb. 2018.
TW Office Action in Application No. 110143123 Dated Oct. 5, 2022.
"Three-part differential of unlabeled leukocytes with a compact lens-free imaging flow cytometer" Lap Chip, Dries Vercruysse, Alexandra Dusa, Richard Stahl, Geert Vanmeerbeeck, Koen de Wijs, Chengxun Liu, Dimiter Prodanov, Peter Peumans and Liesbet Lagae, Dec. 15, 2014.

* cited by examiner (a)

(b)

(c)

(d)

(e)

(A)

(B)

(A)

(B)

METHOD OF TRAINING AI FOR LABEL-FREE CELL VIABILITY DETERMINATION AND LABEL-FREE CELL VIABILITY DETERMINATION METHOD BY TRAINED AI

CROSS-REFERENCE TO RELATED APPLICATIONS

This application claims priority under 35 U.S.C. § 119(a) on Patent Application No(s). 110143123 filed in Taiwan, R.O.C. on Nov. 19, 2021, the entire contents of which are hereby incorporated by reference.

BACKGROUND

1. Technical Field

This present disclosure relates to label-free cell viability determination.

2. Related Art

In the past, tumor treatment in the medical field includes surgery, radiotherapy, chemotherapy, target therapy, and so on. However, the low specificity of traditional chemotherapy may easily kill healthy cells outside the tumor, resulting in systemic adverse side effects. Recently, immunotherapy has been developed as a new therapy for cancer.

Immunotherapy involves drugs, cell therapy and vaccines. Among the various ways of immunotherapy, T cell immunotherapy can recognize and kill tumors more efficiently by using chimeric antigen receptor T cells (CAR-T cells), and CAR-T cells can be derived from genetic engineering of $\alpha\beta T$ or $\gamma\delta T$ immune cells. Production of CAR-T cells for T cell immunotherapy includes collection of T cells from patient, separation of T cells from blood, genetic engineering, and cell proliferation. Since CAR-T cells will be infused back into patient's body, a label-free, non-destructive technique for measuring the cell viability of the CAR-T cells is needed before these CAR-T cells are infused back into patient's body.

SUMMARY

According to one embodiment of the present disclosure, a method of training artificial intelligence (AI) for label-free cell viability determination includes the following steps: providing a cell sample; obtaining a fluorescence image and a digital holographic microscopy (DHM) image of the cell sample; determining a first cell viability of the cell sample according to the fluorescence image of the cell sample; labeling the DHM image of the cell sample as a model specifying the first cell viability; and performing AI training by using the model containing the DHM image of the cell sample.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawings.

Figure 1:
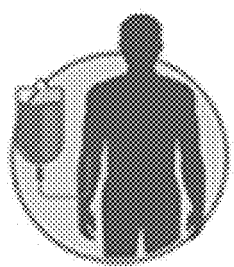
FIG. 1 is a schematic view of immunotherapy.
Figure 1:
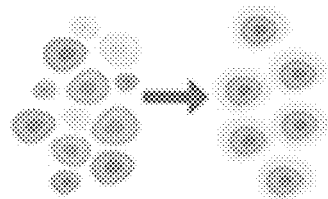
Figure 1:
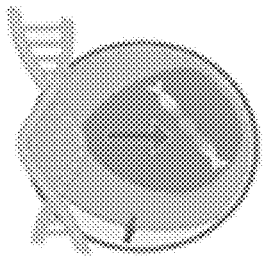
Figure 1:
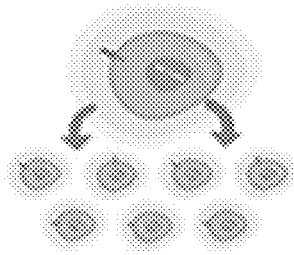
Figure 1:
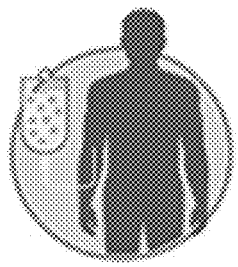

Please refer to FIG. 1, which is a schematic view of immunotherapy. Herein, the exemplary immunotherapy may be T cell activation immunotherapy including the following steps: collecting blood from patient's body (picture (a) in FIG. 1); separating T cells from the blood (picture (b) in FIG. 1); genetically engineering the T cells to produce CAR-T cells (picture (c) in FIG. 1); harvesting and growing the CAR-T cells (picture (d) in FIG. 1); and infusing the CAR-T cells into patient's body (picture (e) in FIG. 1). After the T cells are genetically engineered to be CAR-T cells or the CAR-T cells are harvested and grown, the CAT-T cells should be monitored to determine its viability and then infused back to the patient's body. After the T cells are genetically engineered to be CAR-T cells, cell viability determination can help to select high quality CAT-T cells for the forthcoming cell culture. After the CAR-T cells are harvested and grown, cell viability determination can help medical crew to decide whether the monitored CAR-T cells are suitable to be infused back to the patient's body. Cell production automation aims to at least automate CAT-T cell viability determination.

The cell viability determination can be classified into labeling type and non-labeling type. As to the labeling type such as fluorescent label and magnetic bead label, it is highly probable to change physical and chemical properties of cells and even lead to cell apoptosis after determination, and thus the labeled CAR-T cells cannot be sent back to the patient's body if a labeling type cell viability determination has been performed. As to the non-labeling type such as Raman scattering, optical coherence tomography (ODT) and DHM, it is more suitable to determine cell viability for living T cells. Among the various non-labeling types, DHM is a better choice due to high sensitivity to phase shift and light intensity caused by cell profile.

With regard to conventional DHM application to cell viability determination, positions and cell viability of cells in the DHM image are generally determined by manual operation. Specifically, the cell activity can be determined by naked eye according to shape, size and other information of each cell image in the DHM image, but it is inefficient and cannot be applied to cell production automation system. Therefore, the present disclosure provides a method for training AI to perform label-free cell viability determination, in order to meet the requirements of DHM imaging application as well as cell production automation. An automatic system with the AI which has been trained can perform automatic CAR-T cell viability determination.

Figure 2:
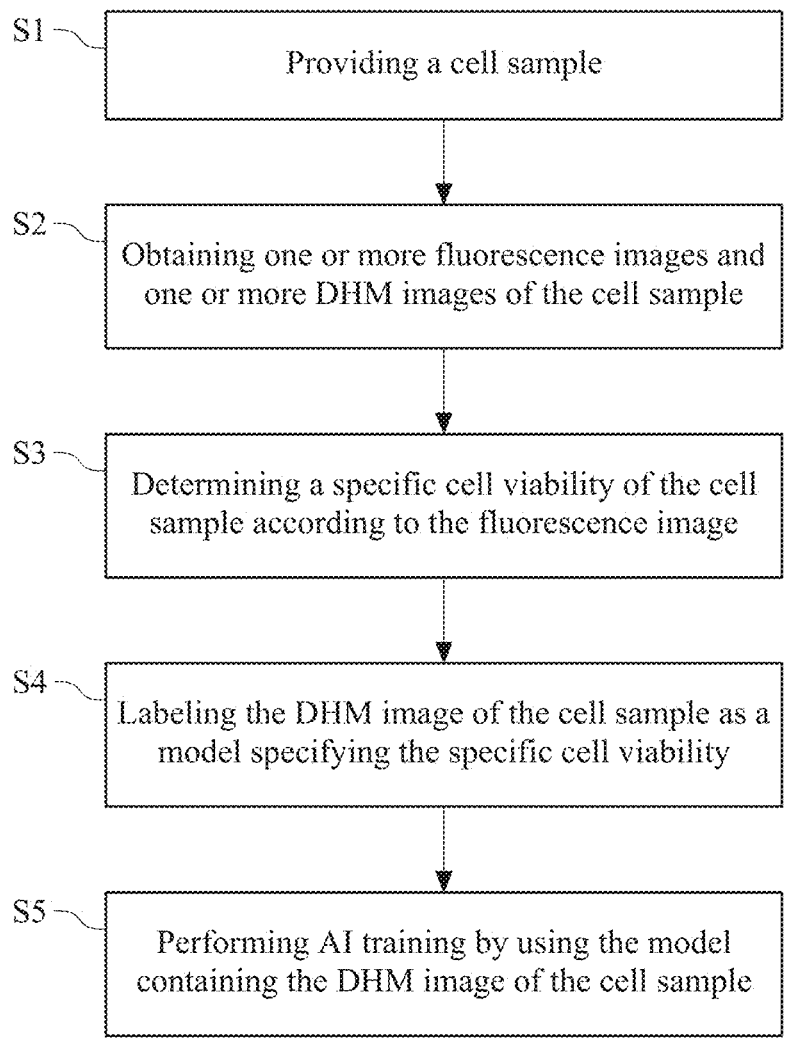
FIG. 2 is a flow chart showing a method of training AI for label-free cell viability determination.

FIG. 2 is a flow chart showing a method of training AI for label-free cell viability determination. The training method includes steps S1 through S5. More specifically, this method is related to how to build training dataset, validation dataset and/or test dataset for AI training.

In step S1, a cell sample is provided. In one embodiment, a CAR-T cell sample including a plurality of living CAR-T cells may be provided. The CAR-T cells may be first generation obtained by genetically engineering of T cells collected from patient's body, or have been harvested and grown. Also, multiple cell samples with different degrees of cell viability may be provided in the step S1; for example, a first CAR-T cell sample and a second CAR-T cell sample may be provided, wherein the first CAR-T cell sample includes fresh CAR-T cells taken from incubator, and the second CAR-T cell sample includes CAR-T cells which has been irradiated with ultraviolet light or rinsed with chlorine solution. Therefore, it is expected that the second CAR-T cell sample has lower cell viability than the first CAR-T cell sample.

Although some manners mentioned above can be used to control the degree of cell viability, it is noting that the cell samples used in the present disclosure are not forced to be processed by these manners, as long as the cell samples use the same reference cell. For example, both the first CAR-T cell sample and the second CAR-T cell includes CAR-T cells obtained by genetically altering human T cells from a patient's body, and the CAR-T cells includes the same CAR receptors.

In the step S2, one or more fluorescence image and one or more DHM image of the cell sample are obtained. In one embodiment, a fluorescence image and a DHM image of the living CAR-T cell sample can be obtained. Specifically, each of the first CAR-T cell sample and the second CAR-T cell including living CAR-T cells may be taken as imaged objects for DHM imaging. For example, part of the CAR-T cell sample is taken to be stained (e.g. PI staining) for capturing fluorescence images, and another part of the CAR-T cell sample is not stained for capturing DHM images. Also, the DHM images are obtained by using a lens-free DHM in the step S2 according to phase shift and light intensity of the captured CAR-T cells. The lens-free DHM has the advantages of compactness, less aberrations and high resolution.

Figure 3:
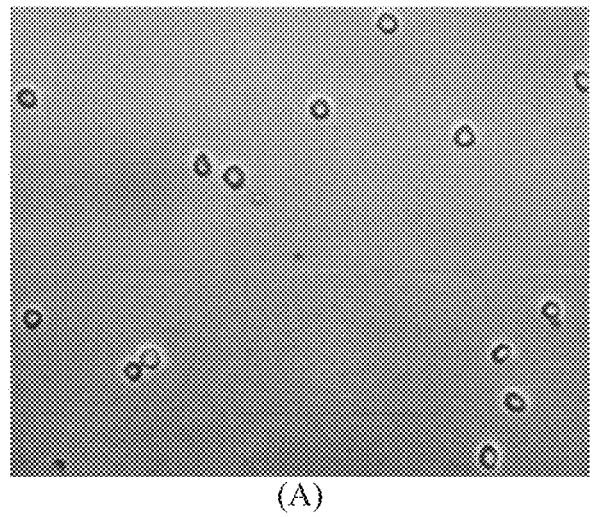
FIG. 3 is exemplary fluorescence images used in the method of FIG. 2.
Figure 3:
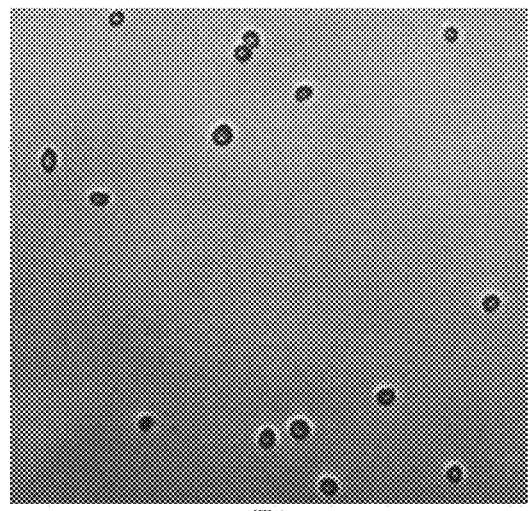

FIG. 3 is exemplary fluorescence images used in the method of FIG. 2. In the step S3, a specific cell viability of the cell sample is determined according to the fluorescence image. In one embodiment, the fluorescence images of the CAR-T cell samples obtained in the step S2 will show different fluorescence signals due to different degrees of cell viability of respective CAR-T cell samples, such that the cell viability can be determined according to the fluorescence signals provided by the CAR-T cells. For example, the degree of cell viability may influence one or more characteristics of the fluorescence signal such as fluorescence intensity and fluorescent color. In one embodiment, most of the captured CAR-T cells in the fluorescence image (image (A) in FIG. 3) related to the first CAR-T cell sample may emit green fluorescent color, and thus the first CAR-T cell sample may be determined to be a cell sample with high cell viability. Similarly, most of the captured CAR-T cells in the fluorescence image (image (B) in FIG. 3) related to the second CAR-T cell sample may emit red fluorescent color, and thus the second CAR-T cell sample may be determined to be a cell sample with low cell viability. Herein, the cell viability may be expressed as "high" or "low" based on the number of cells emitting particular fluorescent color or having particular fluorescence in the fluorescence image, while the cell viability can be expressed as quantified parameters in some other embodiments; for example, the first CAR-T cell sample may be determined to have 98% cell viability, and the second CAR-T cell sample may be determined to have 1% cell viability.

Figure 4:
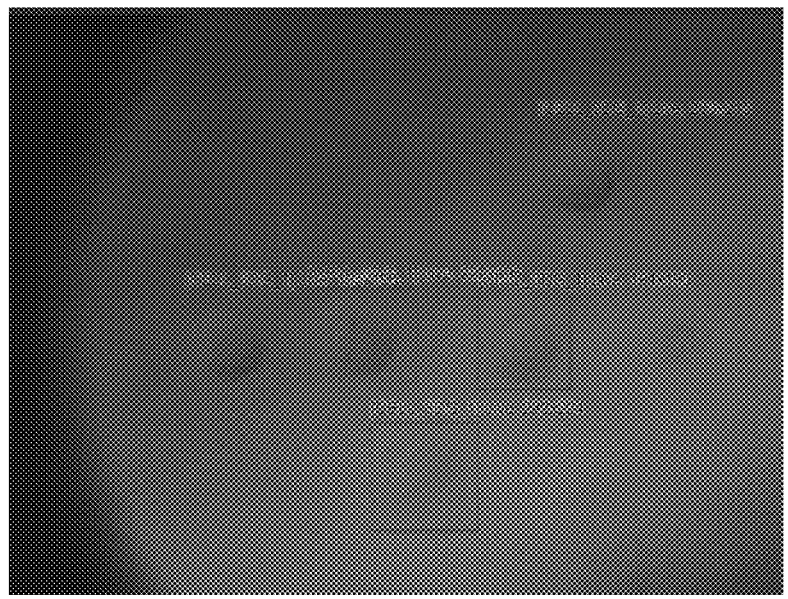
FIG. 4 is an exemplary DHM images used in the method of FIG. 2.
Figure 4:
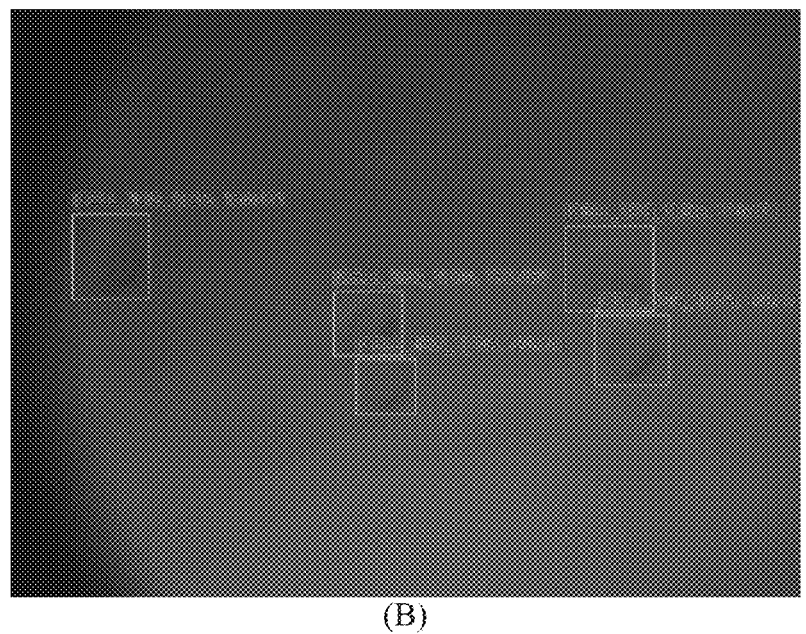

FIG. 4 is an exemplary DHM images used in the method of FIG. 2. In the step S4, the DHM image of the cell sample is labeled as a model specifying the specific cell viability. In one embodiment, the DHM images of the CAR-T cell samples obtained in the step S2 each include a plurality of living CAR-T cells, and the DHM images can be labeled according to the degree of cell viability determined in the step S3. Specifically, the DHM image of the first CAR-T cell sample may be labeled as a model specifying high cell viability according to the determination of cell viability in the step S3 based on the fluorescence image of the first CAR-T cell sample, and the DHM image of the second CAR-T cell sample may be labeled as a model specifying low cell viability according to the determination of cell viability in the step S3 based on the fluorescence image of the second CAR-T cell sample.

In the step S5, an AI training is performed by using the model containing the DHM image of the cell sample. In one embodiment, all CAR-T cell images in the DHM image of the first CAR-T cell sample are considered to include characteristics related to high cell viability, and that in the DHM image of the second CAR-T cell sample are considered to include characteristics related to low cell viability. The DHM images of the first CAR-T cell sample and the second CAR-T cell sample are provided as database for AI machine learning. Once the AI has been trained, the AI can be used to determine that the CAR-T cell images in the DHM image should be classified into high cell vitality group or low cell vitality group.

The term "DHM image" used herein is directed to a DHM image including a plurality of CAR-T cells captured by DHM imaging, as shown in FIG. 4. Moreover, the term "CAR-T cell image" used herein is directed to an image of single CAR-T cell in the DHM image.

The AI machine learning of the present disclosure includes supervised learning and semi-supervised learning. After receiving some labeled DHM images specifying specific degree of cell viability, the machine learning model can forecast the likelihood of characteristics in the labeled DHM images representing the specific degree of cell viability according to the light intensity and phase shift of cell images in these DHM images, thereby building a learning model. When the AI receives DHM images where the cell viability of captured cells is unknown, this model can output regression analysis (for example, a metric for quantifying the cell viability) or forecast classification (for example, the DHM image is classified into high cell viability group or low cell viability group). Methods widely used for classification includes, but not limited to, neural network, support-vector machine, nearest neighbors algorithm, Gaussian mixture model, Naive Bayesian algorithm, decision tree and radial basis function.

Suppose a condition that the AI is trained by a method using DHM imaging in which the cell viability of captured CAR-T cells in the DHM image is determined in a conventional manual manner, the most straightforward idea for labeling one DHM image would be a determination of cell viability directly according to the CAR-T cell images in this DHM image. However, in practice, parameters needed for determining cell viability directly based on DHM image may include not only quantifiable factors, such as phase shift and light intensity, but also some non-quantifiable factors for enhancing accuracy such as overall CAR-T cell size in the DHM image and CAR-T cell morphology in the DHM image.

Determination of the non-quantifiable factors usually depends on practical experiences and is difficult to be implemented by a machine. Therefore, if a DHM image should be labeled directly base on a determination of cell viability according to the CAR-T cell images in this DHM image, it is necessary to individually determine cell viability for each CAR-T cell image in this DHM image, which is quite time-consuming and leads to poor efficiency for machine learning.

In contrast to the previous condition, the method of training AI disclosed herein uses one or more fluorescent images to determine cell viability of the CAR-T cells and labels one or more DHM images as a model specifying high cell viability or low cell viability based on the determination. In the subsequent machine learning procedure, all CAR-T cell images in the DHM image labeled as high cell viability model are regarded as CAR-T cell images including characteristics related to high cell viability, and all CAR-T cell images in the DHM image labeled as low cell viability model are regarded as CAR-T cell images including characteristics related to low cell viability. Although this method may inevitably regard a CAR-T cell image in the DHM image, which is actually an image of single CAR-T cell with low cell viability, as that including high cell viability characteristics, or regard a CAR-T cell image in the DHM image, which is actually an image of single CAR-T cell with high cell viability, as that including low cell viability characteristics, the DHM image labeling according to cell viability determination based on fluorescent image disclosed herein can greatly improve the efficiency of machine learning, or rather, this DHM image labeling can enable the application of DHM imaging to AI machine learning.

The present disclosure also provides a label-free cell viability determination method, wherein a cell viability of a subject cell sample is determined by an AI according to a DHM image of the subject cell sample, and the AI has been trained by the aforementioned method. Take the aforementioned CAR-T cells as an example. The trained AI can identify high cell viability characteristics or low cell viability characteristics of the CAR-T cell images in the DHM image. After one or more DHM images of a subject CAR-T cell sample are delivered to the AI, the number of the CAR-T cells with high cell viability and that of CAR-T cells with low cell viability in the DHM image can be obtained according to the characteristics of the CAR-T cell images in the DHM image, and then the cell viability of the subject CAR-T cell sample can be determined.

The present disclosure observes that the performance of cell viability determination the AI trained by the above method meets actual requirements. The trained AI by the above method using a total of 50 labeled DHM images can have at least 81.27% accuracy, which means that only about 20% of all CAR-T cell images in the DHM image of the subject cell sample may suffer wrong determination of cell viability.

According to the present disclosure, a DHM image labeled as a model specifying a cell viability of a cell sample is provided as database for AI training. The cell viability of the cell sample is firstly determined according to a fluorescence image of the cell sample, and then this determination is applied to label the DHM image as high/low cell viability model. In the subsequent machine learning procedure, all CAR-T cell images in the DHM image labeled as high/low cell viability model are regarded as CAR-T cell images including characteristics related to high/low cell viability. Therefore, it is favorable for improving the efficiency of machine learning, and thus the DHM imaging can be applied to AI training.

It will be apparent to those skilled in the art that various modifications and variations can be made to the present disclosure. It is intended that the specification and examples be considered as exemplary embodiments only, with a scope of the disclosure being indicated by the following claims and their equivalents.

What is claimed is:

1. A method of training artificial intelligence (AI) for label-free cell viability determination, comprising:
providing a cell sample;
obtaining a fluorescence image and a digital holographic microscopy (DHM) image of the cell sample;
determining a first cell viability of the cell sample according to the fluorescence image of the cell sample;
labeling the DHM image of the cell sample as a model specifying the first cell viability; and
performing AI training by using the model containing the DHM image of the cell sample,
the method of training artificial intelligence (AI) for label-free cell viability determination further comprising:
providing another cell sample using same reference cell as the cell sample;
obtaining a fluorescence image and a DHM image of the another cell sample;
determining a second cell viability of the another cell sample according to the fluorescence image of the another cell sample, wherein the second cell viability has different degree from the first cell viability;
labeling the DHM image of the another cell sample as a model specifying the second cell viability; and
performing AI training by using the model containing the DHM image of the another cell sample.

2. The method according to claim 1, wherein a plurality of cells are captured in both the DHM image of the cell sample and the DHM image of the another cell sample.

3. The method according to claim 1, wherein the DHM images are obtained by using a lens-free DHM.

4. The method according to claim 3, wherein the lens-free DHM generates the DHM images according to phase shift and light intensity of captured cells.

5. The method according to claim 1, wherein the DHM images are obtained by capturing living cells in the cell sample and the another cell sample.

6. The method according to claim 1, wherein the cell sample comprises CAR-T (Chimeric antigen receptor T) cells.

7. A label-free cell viability determination method, comprising: determining a cell viability of a subject cell sample by an AI according to a DHM image of the subject cell sample, wherein the AI is trained by the method according to claim 1.

8. The label-free cell viability determination method according to claim 7, wherein the DHM image is obtained by capturing living cells in the subject cell sample.

9. The label-free cell viability determination method according to claim 7, wherein the subject cell sample comprises CAR-T cells.

* * * * *